United States Patent
Allen

(10) Patent No.: US 10,398,850 B2
(45) Date of Patent: Sep. 3, 2019

(54) NEEDLE SHIELD PULLER

(71) Applicant: West Pharmaceutical Services, Inc., Exton, PA (US)

(72) Inventor: Timothy Allen, Scottsdale, AZ (US)

(73) Assignee: West Pharmaceutical Services, Inc., Exton, PA (US)

(*) Notice: Subject to any disclaimer, the term of this patent is extended or adjusted under 35 U.S.C. 154(b) by 0 days.

(21) Appl. No.: 16/075,325

(22) PCT Filed: Feb. 8, 2017

(86) PCT No.: PCT/US2017/017016
§ 371 (c)(1),
(2) Date: Aug. 3, 2018

(87) PCT Pub. No.: WO2017/139377
PCT Pub. Date: Aug. 17, 2017

(65) Prior Publication Data
US 2019/0060580 A1    Feb. 28, 2019

Related U.S. Application Data

(60) Provisional application No. 62/292,552, filed on Feb. 8, 2016.

(51) Int. Cl.
*A61M 5/32*    (2006.01)

(52) U.S. Cl.
CPC ... *A61M 5/3204* (2013.01); *A61M 2205/0216* (2013.01); *A61M 2209/04* (2013.01)

(58) Field of Classification Search
CPC .............. A61M 5/3202; A61M 5/3204; A61M 2205/0216; A61M 25/005; A61M 2209/04; A51M 2005/3247
See application file for complete search history.

(56) References Cited

U.S. PATENT DOCUMENTS

| | | |
|---|---|---|
| 4,334,536 A | 6/1982 | Pfleger |
| 4,430,082 A | 2/1984 | Schwabacher |

(Continued)

FOREIGN PATENT DOCUMENTS

| | | |
|---|---|---|
| EP | 2878322 A1 | 6/2015 |
| WO | 9007944 A1 | 7/1990 |

OTHER PUBLICATIONS

International Preliminary Report on Patentablity dated Jun. 6, 2018 in International Application No. PCT/US2017/017016.

(Continued)

*Primary Examiner* — Imani N Hayman
*Assistant Examiner* — Tiffany Legette
(74) *Attorney, Agent, or Firm* — Panitch Schwarze Belisario & Nadel LLP

(57) ABSTRACT

A needle shield puller has a deformable tubular body including a proximal end having a proximal opening and a distal end. An opening extends from the proximal opening toward the distal end. The opening is shaped to accommodate a portion of a needle shield. The body has initial and tension states and the opening diameter is greater in the initial state. A cinch is secured to the body at the proximal opening to secure the needle shield puller to the needle shield. The cinch biases the cinch diameter to a relaxed cinch diameter less than the needle shield diameter. A handle at a distal end of the body allows a user to place the body in the tension state. An installation aid comprises an arm releasably engageable with the cinch and the proximal opening to expand the cinch diameter toward a maximum cinch diameter greater than the needle shield diameter.

20 Claims, 4 Drawing Sheets

(56) References Cited

U.S. PATENT DOCUMENTS

| | | | |
|---|---|---|---|
| 5,078,697 A | | 1/1992 | Rammler |
| 5,472,450 A | * | 12/1995 | Mena ................... A61B 17/282 294/99.2 |
| 5,480,203 A | | 1/1996 | Favalora et al. |
| 5,593,413 A | | 1/1997 | Alexander |
| 5,649,541 A | | 7/1997 | Stuckey |
| 5,702,369 A | | 12/1997 | Mercereau |
| 6,431,864 B1 | * | 8/2002 | Silverstein ............... A61C 3/10 433/159 |
| 7,141,286 B1 | * | 11/2006 | Kessler ............... A61M 5/3202 428/41.8 |
| 9,339,609 B2 | | 5/2016 | Ekman et al. |
| 2002/0062108 A1 | * | 5/2002 | Courteix ............. A61M 5/3202 604/198 |
| 2006/0270986 A1 | | 11/2006 | Hommann et al. |
| 2007/0049901 A1 | * | 3/2007 | Wu ................... A61M 37/0015 604/506 |
| 2012/0216335 A1 | | 8/2012 | McKenna, Jr. et al. |
| 2014/0353561 A1 | | 12/2014 | Chen et al. |
| 2015/0182691 A1 | * | 7/2015 | McLoughlin ......... A61M 5/002 604/155 |

OTHER PUBLICATIONS

Int'l Search Report and Written Opinion dated Jun. 8, 2017 in Int'l Appn. No. PCT/US17/17016.

* cited by examiner

NEEDLE SHIELD PULLER

CROSS-REFERENCE TO RELATED APPLICATIONS

The present application is a Section 371 of International Application No. PCT/US17/17016, filed Feb. 8, 2017, which was published in the English language on Aug. 17, 2017 under International Publication No. WO 2017/139377 A1 and titled, "Braided Needle Shield Puller," which claims the benefit of U.S. Provisional Patent Application No. 62/292,552, filed Feb. 8, 2016. The entire contents of both applications identified in this section are incorporated herein by reference.

BACKGROUND OF THE INVENTION

The present invention is related generally to hypodermic needles and, more particularly, to a needle shield puller for removing a needle shield from a syringe. The needle shield puller is preferably adapted to remove a needle shield from a variety of syringes which may have differently sized or shaped needle shields.

Hypodermic needles generally include a needle assembly and a needle shield. The needle shield covers the needle assembly prior to using the syringe to protect the needle from damage caused by outside forces and to protect against inadvertent needle "sticks" prior to and after injection of the medication. The needle shield is removed at the time of use to expose the sharp point of the needle, which can inflict injury if the user inadvertently is stuck or pricked. For example, if the needle shield contacts the needle as the shield is being removed, the needle can "spring back" and stick the user. Devices are often used to remove the needle shield from the needle assembly to avoid the risk of inadvertent sticks. Care must be taken when using such devices to avoid damaging the needle shield and the needle assembly while removing the "needle shield". There are many different types of needle shields commercially available, including a wide variety of devices that may only remove a single needle shield design.

It would be advantageous to design, develop, construct and deploy a needle shield puller capable of removing a variety of needle shields of differing sizes and shapes while minimizing or eliminating compressive forces exerted during removal of the needle shield from the syringe, thereby preventing needle sticks and needle damage.

BRIEF SUMMARY OF THE INVENTION

Briefly stated, a needle shield puller for removing a needle shield, having a needle shield diameter, from a syringe having a needle and a longitudinal axis includes a deformable, generally tubular body. The body has a proximal end with a proximal opening, a distal end, and an opening extending from the proximal opening toward the distal end. The opening has an opening diameter and is shaped to accommodate at least a portion of the needle shield. The body has an initial state and a tension state and is configured such that the opening diameter is greater in the initial state than in the tension state. A cinch is secured to the body at the proximal opening to secure the needle shield puller to the needle shield in a mounted configuration. The cinch has a cinch diameter and biases the cinch diameter to a relaxed cinch diameter. The relaxed cinch diameter is less than the needle shield diameter. The needle shield puller also comprises a handle at a distal end of the body. The handle is graspable to allow a user to exert a tensile force on the body and place the body in the tension state. An installation aid comprises an arm releasably engageable with the cinch and the proximal opening. The installation aid is graspable by the user for pulling in a direction radially away from the longitudinal axis in a mounted configuration to expand the cinch diameter toward a maximum cinch diameter. The maximum cinch diameter is greater than the needle shield diameter.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
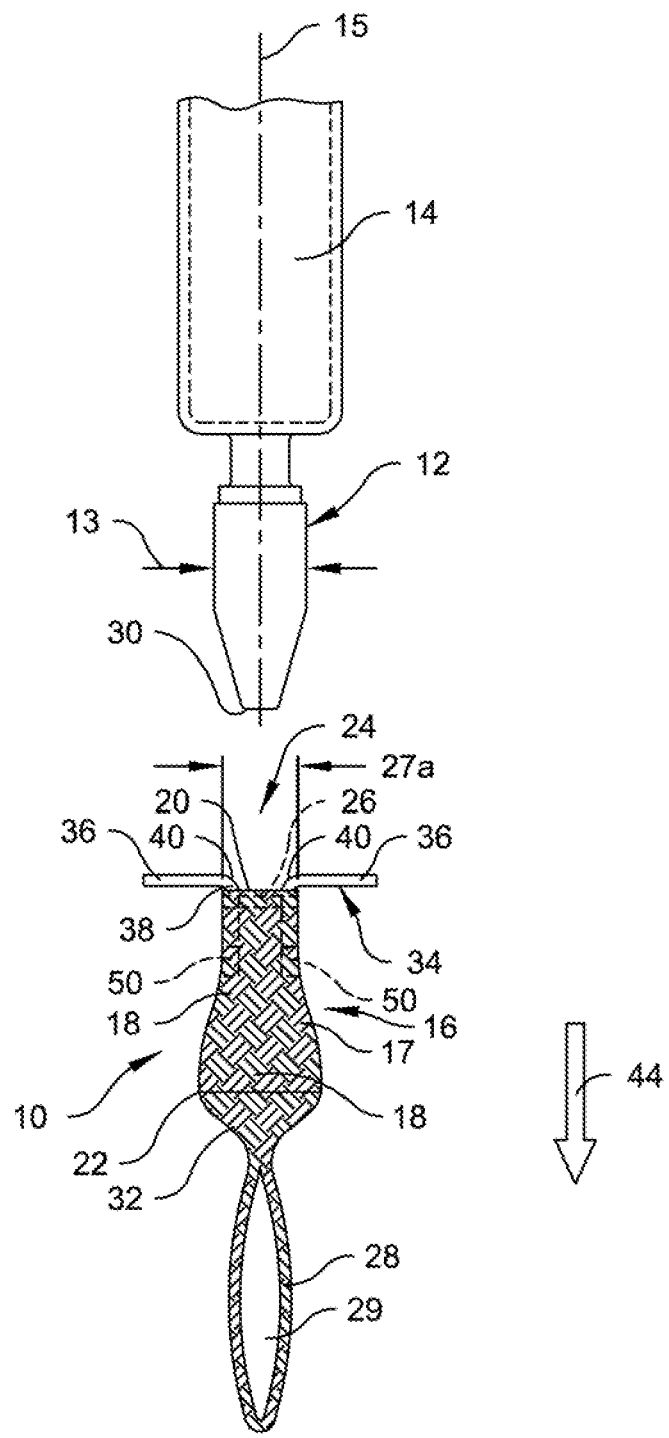
FIG. 1 is a front elevational view of a needle shield puller in accordance with a preferred embodiment of the present invention, wherein the needle shield puller is positioned proximate a needle shield and a syringe.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the geometric center of the device and related parts thereof. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, FIGS. 1-4 illustrate a needle shield puller, generally identified with reference numeral 10, in accordance with a preferred embodiment of the present invention. The needle shield puller 10 is preferably used to remove a needle shield 12 from a syringe 14 without damaging the needle or causing inadvertent needle sticks. The needle shield 12 and the syringe 14 share a longitudinal axis 15 in a mounted configuration (FIGS. 1-4). The needle shield 12 has a needle shield diameter 13, which is the largest diameter of a preferably round needle shield 12, or alternatively is the length between the two most distant points on a given cross-section of a needle shield 12, where the needle shield 12 is not round in cross-section and the cross-section is taken perpendicular to a longitudinal axis of the needle shield 12. The needle shield puller 10 includes a deformable, generally tubular body 16 that preferably conforms to the shape of any needle shield 12 that may be positioned within the body 16 to apply a generally uniform force on an exterior surface of the needle shield 12 as it is removed. This allows a single needle shield puller 10 to be used with a wide variety of differently sized or shaped needle shields 12. In other words, the preferred present invention reduces the need for a clinician to stock multiple needle shield pullers 10, each of which can only be used with a single type of needle shield 12.

The body 16 of the preferred needle shield puller 10 is constructed of a braided tube made of a plurality of flexible fibers 18 (e.g. nylon, fiberglass, or cotton, alone or in combination) woven together to form the tubular body 16. As should be understood by one of ordinary skill in the art based on a review of the present disclosure, any type of weaving pattern (e.g. basket weave, plain weave, twill) is useable provided that the body 16 collapses to engage the needle shield 12 as a force is applied to one end of the body 16, similar to a Chinese finger trap. It is preferable, but not required, that the fibers 18 are woven in such a way that the body 16 can return to its original shape on its own after the force is no longer applied to the body 16 or at least the body 16 can be returned to its original shape by applying a different, restorative force.

The woven fibers 18 define an opening 24, which is preferably cylindrical, extending from a proximal end 20 toward a distal end 22 of the body 16. Alternatively, the opening 24 can have any suitable geometrical shape provided that at least a portion (and preferably all or most) of a needle shield 12 fits within the opening 24. The opening 24 is shaped to accommodate at least a portion of the needle shield 12, or a range of differently sized needle shields. The opening 24 has an opening diameter 25, which preferably approximates or is slightly larger than the size of the needle shield 12 or a range of needle shields with which the needle shield puller 10 may be used. The opening diameter 25 may be constant or variable along the length of the opening 24 between the proximal end 20 and the distal end 22. The opening diameter 25 is not limited to being approximately the same or a similar size relative to the size of the needle shield 12, as the size and shape of the opening 24 is expanded, modified and contracted during use of the needle shield puller 10, as is described in further detail below. Thus, a single needle shield puller 10 is preferably able to remove any needle shield 12 that fits within the opening 24.

The body 16 has an initial state and a tension state corresponding to stretching of the body 16 along the longitudinal axis 15. The body 16 is preferably configured such that the opening diameter 25 is greater in the initial state than in the tension state.

Figure 3:
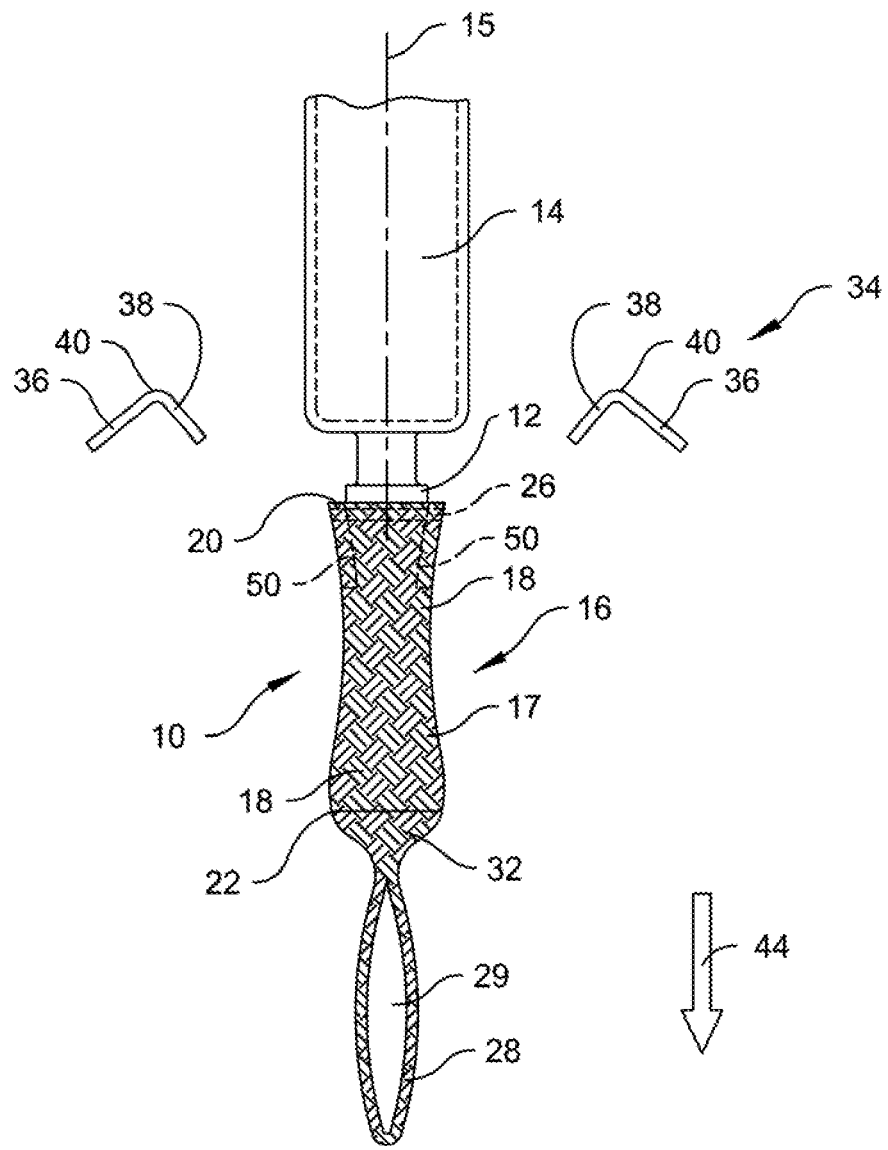
FIG. 3 is a front elevational view of the needle shield puller of FIG. 1, wherein the needle shield puller is mounted on the needle shield.
Figure 4:
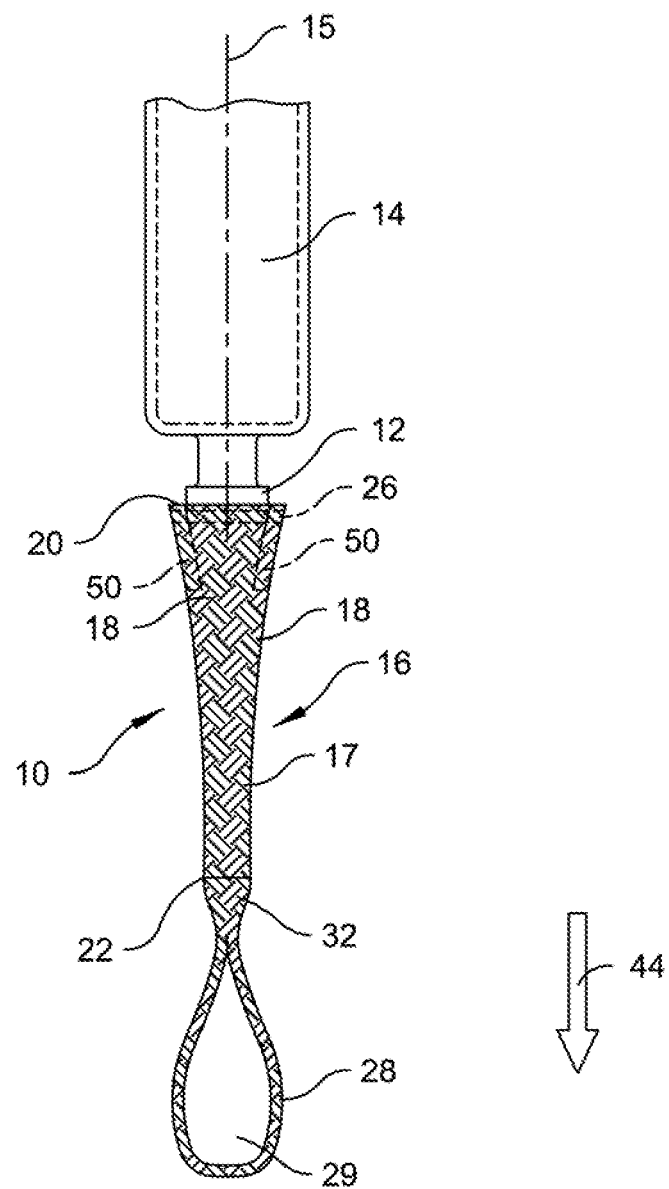
FIG. 4 is a front elevational view of the needle shield puller of FIG. 1, wherein the needle shield puller is mounted on the needle shield and a force is applied to a cord-like handle of the needle shield puller.

A cinch 26 is secured to the body 16 at the opening 24. The cinch 26 is preferably positioned near the proximal end 20 of the body 16 to secure the needle shield puller 10 to the needle shield 12 in a mounted configuration (FIGS. 3 and 4). The cinch 26 preferably has a cinch diameter 27 and biases the cinch diameter 27 to a relaxed cinch diameter 27a (FIG. 1), which is less than the shield diameter 13, as shown in FIGS. 1 and 4. The cinch 26 is preferably comprised of an elastic band but could also be any element capable of at least temporarily securing the needle shield puller 10 to the needle shield 12 (e.g. a belt, zip tie, drawstring, Velcro band, adhesive). The fibers 18 of the body 16 are preferably woven around the cinch 26 to secure or connect the cinch 26 to the body 16. Alternatively, the cinch 26 can be otherwise attached to the body 16, such as by being secured to the fibers 18 near the opening 24 or otherwise attached to a portion of the body 16 by adhesive bonding, stapling, clamping, fastening, stitching or other related attachment methods or mechanisms.

The needle shield puller 10 preferably includes a cord-like handle 28 at the distal end 22 of the body 16. The handle 28 is graspable to allow the user to apply a tensile force to the body 16 of the needle shield puller 10 and place the body 16 in the tension state. Alternatively, the handle 28 may be comprised of any graspable device or feature (not shown but could be, a sling, a bar, a ring, a tab, etc.) that allows the user to apply a force to the body 16. In another alternative embodiment (not shown), the needle shield puller 10 does not have a handle 28 but instead includes an elongated body 16 having an exterior surface 17 such that the body 16 extends beyond a distal end 30 of the needle shield 12 in the mounted configuration. In this alternative embodiment, the exterior surface 17 at the distal end 22 of the body 16 itself may be utilized as the handle. In the preferred embodiment, the fibers 18 which form the body 16 also form the handle 28 using weaving methods to integrally form the handle 28 with the body 16. The preferred handle 28 forms a finger hole 29 for engaging one or more fingers of the user. Alternatively (not shown), the handle 28 may be comprised of a separate element formed from any desired material such as metal, plastic, polymeric, nylon, fiberglass, etc. with the fibers 18 connected by engaging methods or mechanisms, such as tying, adhesive bonding, fastening, clamping, hooking or other related methods or mechanisms. A taper 32 is preferably formed by the fibers 18 at the distal end of the body 16 to couple the handle 28 to the body 16. The taper 32 preferably provides a uniform force on the fibers 18 when a force is applied to the handle 28 in the tension state.

The needle shield puller 10 also includes an installation aid 34 to expand the cinch 26 and the opening 24 when positioning the body 16 about the needle shield 12. The installation aid 34 of the preferred embodiment comprises a pair of removable, generally L-shaped arms 36 releasably engageable with the cinch 26, the proximal end 20 of the body 16 or with both the cinch 26 and the proximal end 20. The engagement may be made by direct contact with the cinch 26 or by indirectly exerting force on the cinch 26, for example, by exerting force on the body 16. The arms 36 are graspable by the user to be pulled in a direction 42 radially away from the longitudinal axis 15 to expand the cinch diameter 27 so that the cinch diameter 27 is greater than the needle shield diameter 13, preferably so as to minimize, or avoid, exerting any compressive forces on the needle shield 12 when installing the needle shield puller 10 on the needle shield 14. The user may then stop exerting force on the cinch 26, allowing the cinch diameter 27 to return to the relaxed cinch diameter 27a. Alternatively, the installation aid 34 may include a single arm 36 or more than two arms 36. Each arm 36 of the preferred embodiment is a generally straight rod or bar which is graspable by a user and has a hand 38 extending generally perpendicularly therefrom that engages the cinch 26 and/or body 16. Alternatively, the arm 36 has any desired shape (e.g. corkscrew, hooked, angled, circular, cylindrical) and is manipulable (e.g. by pulling, pushing, twisting) to expand the cinch 26 and the opening 24.

The hand 38, or the entire installation aid 34, is preferably constructed of a rigid material (e.g. plastic, metal) to withstand the forces necessary to expand the cinch 26. Alternatively, the fibers 18 also form the installation aid 34 (not shown) using the same or similar weaving techniques as that used to create the body 16. The hand 38 of the preferred installation aid 34 includes a length in a proximal to distal direction 44 preferably greater than or equal to the length of the cinch 26 measured in the same direction 44 so the force is applied along an entire cross-section of the cinch 26. A pulling force is applied to the installation aid 34 to avoid placing any compressive force on the needle shield 12. However, the arm 36 can be used as a lever to rotate the hand 38 about a fulcrum 40 that presses against the needle shield 12 to provide a mechanical advantage to the user when manipulating the installation aid 34 to position the needle shield 12 within the opening 24. Such a design is beneficial for users with minimal hand strength to manipulate the installation aid 34.

The installation aid 34 is preferably formed separately from the body 16 and positioned within the opening 24, but is not so limited and the installation aid 34 may be integrally formed with the body 16. Pockets 50 may be formed at the proximal end 20 of the body 16 near the opening 24 to receive the hands 38. Alternatively, the installation aid 34 can have a frangible connection, such as an adhesively lined pocket 50, connecting the installation aid 34 to the body 16, or a frangible connection (not shown) to the cinch 26 such that the installation aid 34 is securely attached to the body 16 or cinch 26 during installation and is removable after installation. In yet another alternative embodiment (not shown), the installation aid 34 can be permanently attached to the body 16 or cinch 26 by adhesive, welding, anchors, integrally forming or other related methods or mechanisms.

Figure 2:
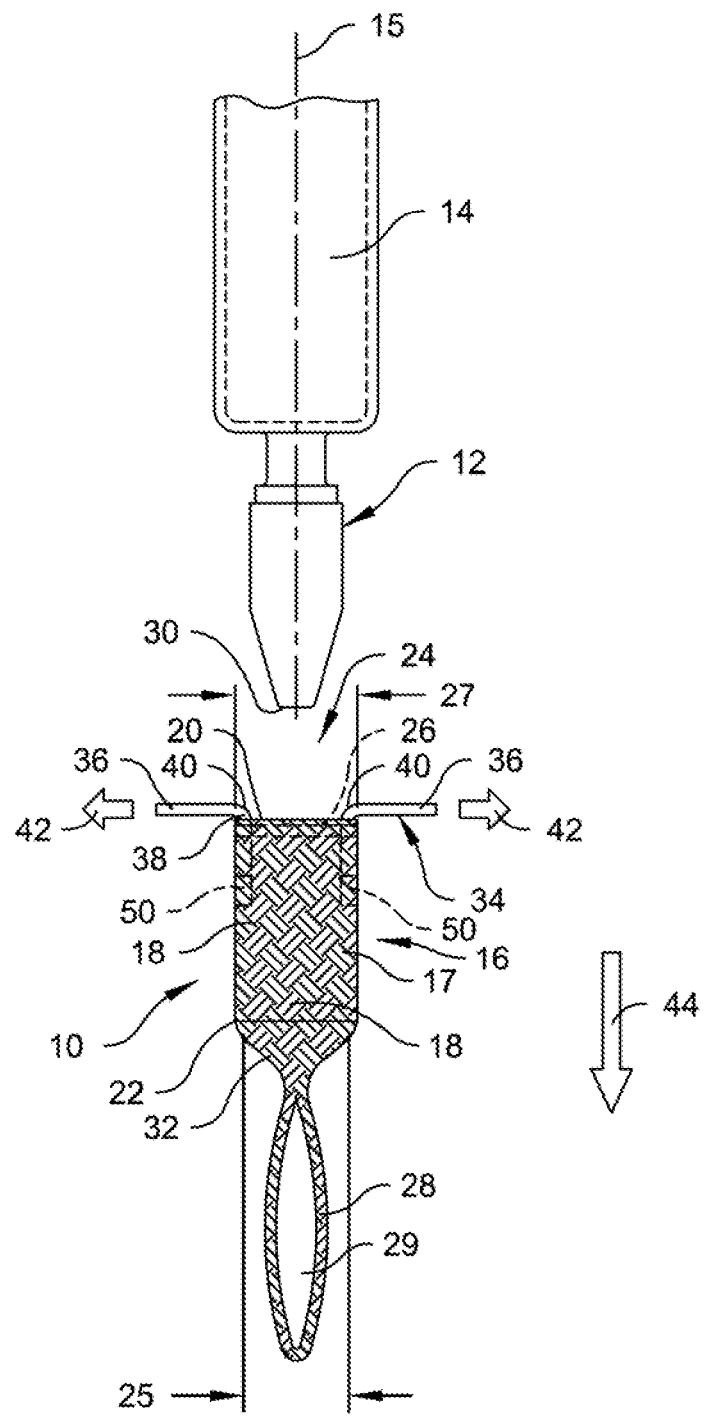
FIG. 2 is a front elevational view of the needle shield puller of FIG. 1, wherein a cinch diameter of a tubular body of the needle shield puller is expanded by arms of the needle shield puller.

In use, the installation aid 34 is connected to the body 16 at the proximal end 20 and a user pulls the installation aid 34 (if needed) to expand the cinch 26 so the opening 24 is at least slightly larger in diameter than the needle shield 12 (FIG. 2). The user then maneuvers the installation aid 34 or syringe 14 to position at least a portion (and preferably most or all) of the needle shield 12 within the opening 24. The entire needle shield 12 is not limited to being positioned within the opening 24, but such arrangement is preferred such that a significant portion of the body 16 surrounds the needle shield 12 in the mounted configuration. The installation aid 34 is then separated from the body 16 and may be saved for later use (FIG. 3). The cinch 26 bears against the needle shield 12 when the installation aid 34 is removed to secure the needle shield puller 10 to the needle shield 12. The user then grasps the handle 28 and begins to apply a force in a direction 44 away from the syringe 14. The cinch 26 maintains the position of the proximal end 20 of the body 16 on the needle shield 12 as the force is applied to the handle 28. The braided pattern of the fibers 18 causes the body 16 to elongate and constrict against the needle shield 12 to firmly "grasp" the needle shield 12 as the force is applied to the handle 28 (FIG. 4). The coupling force between the body 16 and the needle shield 12 is enhanced as the body 16 elongates. Continued application of the pulling force on the handle 28 overcomes the frictional force holding the needle shield 12 on the syringe 14 and the needle shield 12 is removed from the syringe 14, preferably moving substantially parallel along the longitudinal axis 15. The force is then preferably released from the handle 28 and the body 16 returns to its relaxed state after the needle shield 12 is removed from the syringe 14. The needle shield 12 is removed from the needle shield puller 10 for reapplication to the syringe 12 after a medication has been dispensed. The needle shield puller 10 is thereafter available for removing a needle shield 12 from another syringe 14.

It will be appreciated by those skilled in the art that changes could be made to the embodiment described above without departing from the broad inventive concepts thereof. It is understood, therefore, that this disclosure is not limited to the particular embodiment disclosed, but it is intended to cover modifications within the spirit and scope of present disclosure, particularly as described in the appended claims.

I claim:

1. A needle shield puller for removing a needle shield having a needle shield diameter from a syringe having a needle and a longitudinal axis, the needle shield puller comprising: a deformable, generally tubular body having a proximal end with a proximal opening, a distal end, and an opening extending from the proximal opening toward the distal end, the opening having an opening diameter and being shaped to accommodate at least a portion of the needle shield, the body having an initial state and a tension state, the body being configured such that the opening diameter is greater in the initial state than in the tension state; a cinch secured to the body at the proximal opening to secure the needle shield puller to the needle shield in a mounted configuration, the cinch having a cinch diameter, the cinch biasing the cinch diameter to a relaxed cinch diameter, the relaxed cinch diameter being less than the needle shield diameter; a handle at the distal end of the body, the handle being graspable to allow a user to exert a tensile force on the body and place the body in the tension state; and an installation aid comprising an arm releasably engageable with the cinch and the proximal opening, wherein the proximal end of the body includes a pocket configured to receive at least a portion of the arm, the installation aid graspable by the user for pulling in a direction radially away from the longitudinal axis in a mounted configuration to expand the cinch diameter so that the cinch diameter is greater than the relaxed cinch diameter and the needle shield diameter.

2. A needle shield puller for removing a needle shield having a needle shield diameter from a syringe having a needle and a longitudinal axis, the needle shield puller comprising: a deformable, generally tubular body having a proximal end with a proximal opening, a distal end, and an opening extending from the proximal opening toward the distal end, the opening having an opening diameter and being shaped to accommodate at least a portion of the needle shield, the body having an initial state and a tension state, the body being configured such that the opening diameter is greater in the initial state than in the tension state; a cinch secured to the body at the proximal opening to secure the needle shield puller to the needle shield in a mounted configuration, the cinch having a cinch diameter, the cinch biasing the cinch diameter to a relaxed cinch diameter, the relaxed cinch diameter being less than the needle shield diameter; a handle at the distal end of the body, the handle being graspable to allow a user to exert a tensile force on the body and place the body in the tension state; and an installation aid comprising an arm releasably engageable with the cinch and the proximal opening, the arm has a generally L-shape, the installation aid graspable by the user for pulling in a direction radially away from the longitudinal axis in a mounted configuration to expand the cinch diameter so that the cinch diameter is greater than the relaxed cinch diameter and the needle shield diameter.

3. The needle shield puller of claim 2, wherein the cinch comprises an elastic band secured to the proximal opening.

4. The needle shield puller of claim 2, wherein woven flexible fibers of the body are woven around the cinch to seal the cinch into the body.

5. The needle shield puller of claim 2, wherein the arm is constructed of woven flexible fibers of the body.

6. The needle shield puller of claim 2, wherein the opening diameter is variable between the proximal end and the distal end.

7. The needle shield puller of claim 2, wherein the handle is constructed from a material selected from the group consisting of metal, plastic, polymeric, nylon, and fiberglass.

8. The needle shield puller of claim 2, wherein the installation aid is connected to the proximal end of the body by a frangible connection.

9. The needle shield puller of claim 2, wherein the body has an exterior surface and the distal end of the body extends beyond the needle shield in the mounted configuration, such that the exterior surface at the distal end of the body forms the handle.

10. The needle shield puller of claim 2, wherein the body is constructed of woven flexible fibers.

11. The needle shield puller of claim 10, wherein the woven flexible fibers are selected from the group consisting of nylon, fiberglass and cotton.

12. The needle shield puller of claim 2, wherein the handle includes a finger hole.

13. The needle shield puller of claim 12, wherein the handle is formed from woven flexible fibers of the body.

14. The needle shield puller of claim 12, wherein the body includes a taper formed by woven flexible fibers at the distal end of the body for coupling the handle to the body.

15. The needle shield puller of claim 2, wherein the arm is constructed of a rigid structural material.

16. The need shield puller of claim 15, wherein the rigid structural material is one of a metal and a plastic material.

17. A needle shield puller for removing a needle shield having a needle shield diameter from a syringe having a needle and a longitudinal axis, the needle shield puller comprising: a deformable, generally tubular body having a proximal end with a proximal opening, a distal end, and an opening extending from the proximal opening toward the distal end, the opening having an opening diameter and being shaped to accommodate at least a portion of the needle shield, the body having an initial state and a tension state, the body being configured such that the opening diameter is greater in the initial state than in the tension state; a cinch secured to the body at the proximal opening to secure the needle shield puller to the needle shield in a mounted configuration, the cinch having a cinch diameter, the cinch biasing the cinch diameter to a relaxed cinch diameter, the relaxed cinch diameter being less than the needle shield diameter; a handle at the distal end of the body, the handle being graspable to allow a user to exert a tensile force on the body and place the body in the tension state; and an installation aid comprising an arm releasably engageable with the cinch and the proximal opening, wherein the installation aid comprises a pair of L-shaped arms releasably engageable with the cinch and the proximal end of the body, the installation aid graspable by the user for pulling in a direction radially away from the longitudinal axis in a mounted configuration to expand the cinch diameter so that the cinch diameter is greater than the relaxed cinch diameter and the needle shield diameter.

18. The needle shield puller of claim 17, wherein the body is constructed of woven flexible fibers.

19. The needle shield puller of claim 18, wherein the woven flexible fibers are selected from the group consisting of nylon, fiberglass and cotton.

20. The needle shield puller of claim 18, wherein the woven flexible fibers are constructed in a weaving pattern, the weaving pattern selected from the group consisting of a basket weave, a plain weave and a twill.

* * * * *

UNITED STATES PATENT AND TRADEMARK OFFICE
CERTIFICATE OF CORRECTION

PATENT NO. : 10,398,850 B2
APPLICATION NO. : 16/075325
DATED : September 3, 2019
INVENTOR(S) : Timothy Allen Page 1 of 1

It is certified that error appears in the above-identified patent and that said Letters Patent is hereby corrected as shown below:

In the Claims

Column 7, Claim number 16, Line number 39, should be corrected as follows:
The needle shield puller of claim 15, wherein the rigid structural material is one of a metal and a plastic material.

Signed and Sealed this
Twenty-seventh Day of October, 2020

Andrei Iancu
*Director of the United States Patent and Trademark Office*